US00PP15172P2

(12) United States Plant Patent
Uchneat

(10) Patent No.: US PP15,172 P2
(45) Date of Patent: Sep. 21, 2004

(54) IMPATIENS PLANT NAMED 'BALPIXOTSE'

(50) Latin Name: *Impatiens walleriana*
Varietal Denomination: Balpixotse

(75) Inventor: Michael Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 14 days.

(21) Appl. No.: 10/736,721

(22) Filed: Dec. 16, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct cultivar of Impatiens plant named 'Balpixotse' characterized by its single, pink-colored flowers, dark green-colored foliage, compact, upright and mounded growth habit, and excellent basal branching.

1 Drawing Sheet

Figure 1:
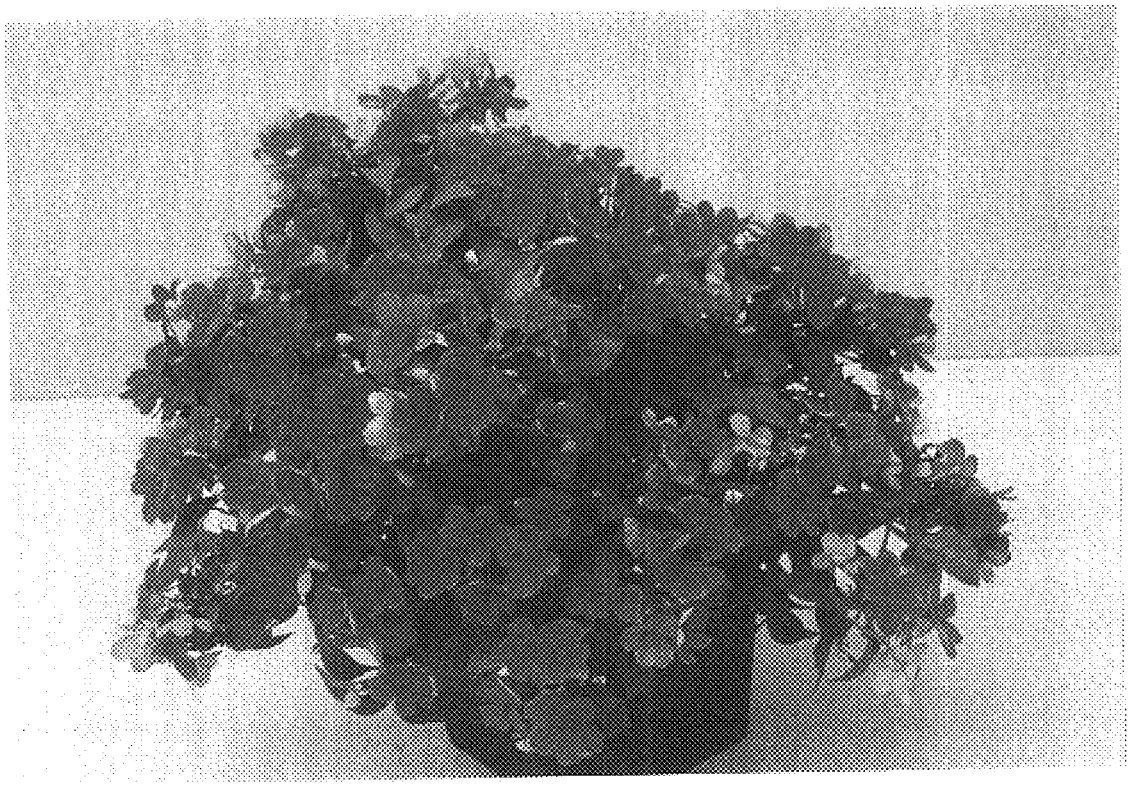

Latin name of the genus and species of plant claimed: *Impatiens walleriana.*
Variety denomination: 'Balpixotse'.

BACKGROUND OF THE INVENTION

The present invention relates to a new and distinct cultivar of Impatiens plant botanically known as *Impatiens walleriana* and hereinafter referred to by the cultivar name 'Balpixotse'.

The new cultivar was developed by the inventor in a controlled breeding program during February 1999 at Elburn, Ill. The objective of the breeding program was to develop new Impatiens cultivars with numerous small flowers, excellent basal branching and upright compact growth habit.

The female (seed) parent of 'Balpixotse' was the proprietary *Impatiens walleriana* selection designated '3264-2' (not patented) characterized by its vigorous growth habit, small, single rose-colored flowers and dark green-colored foliage. The male (pollen) parent of 'Balpixotse' was the proprietary *Impatiens walleriana* selection '3275-1' (not patented) characterized by its compact growth habit, fully double dark purple-colored flowers and dark green-colored foliage. 'Balpixotse' was discovered and selected as one flowering plant within the progeny of the stated cross-pollination in November of 1999 and was initially designated PAS '11915-3'.

Asexual reproduction of the new cultivar by terminal cuttings in Elburn, Ill. and West Chicago, Ill., has demonstrated that the characteristics of the new cultivar, as herein described, reproduce true to type and are firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any change in phenotype.

It was repeatedly found that the cultivar of the present invention:

1. Exhibits small, single pink-colored flowers,
2. Forms dark green-colored foliage,
3. Exhibits a good basal branching character, and
4. Exhibits a compact, upright and mounded growth habit.

Plants of the new cultivar differ from plants of the female parent primarily in growth habit and from plants of the male parent primarily in flower type and flower color.

Of the many commercially available Impatiens cultivars known to the inventor, the most similar to 'Balpixotse' is 'Fify Violet' (U.S. Plant Pat. No. 11,557). In side-by-side comparison, plants of the new cultivar differ from plants of 'Fify Violet' by the following characteristics:

1. Plants of 'Balpixotse' have rose pink-colored flowers whereas plants of 'Fify Violet' have purple-colored flowers, and
2. Plants of 'Balpixotse' have a more vigorous growth habit than plants of 'Fify Violet'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balpixotse'. The plants were grown for 8 weeks in a greenhouse at West Chicago, Ill.

FIG. 1 illustates a side view of the general growth and flowering habit of 'Balpixotse'.

Figure 2:
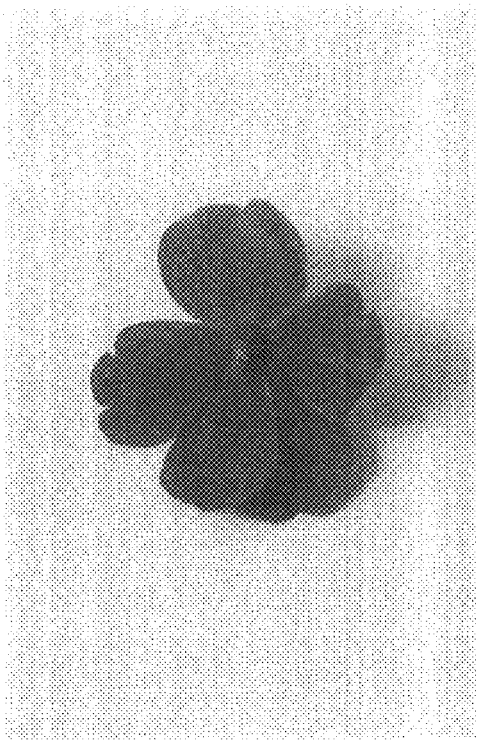

FIG. 2 illustrates a close-up vies of a single flower of 'Balpixotse'.

DETAILED DESCRIPTION

The chart used in the identification of colors described herein is The R.H.S. Colour Chart of The Royal Horticultural Society, London, England, 1995 edition, except where general color terms of ordinary significance are used. The color values were determined on Aug. 8, 2003 between 10:00 and 11:45 a.m. under natural daylight conditions.

The following measurements and comparisons describe plants produced from cuttings taken from stock plants and grown under greenhouse conditions comparable to those used in commercial practice. Plants were grown in 10 cm pots for 8 weeks while utilizing a soilless growth medium. Greenhouse temperatures were maintained at approximately 65°–75° F. during the day and approximately 55°–62° F. during the night. Greenhouse light levels were maintained at approximately 4,000–6,000 footcandles during the day.

Classification: Botanical — *Impatiens walleriana* cultivar 'Balpixotse'.

Parentage:

*Female (seed) parent.*—Proprietary *Impatiens walleriana* selection designated '3264-2' (not patented).

*Male (pollen) parent.*—Proprietary *Impatiens walleriana* selection designated '3275-1' (not patented).

Propagation:

*Type cutting.*—Terminal tip.

*Time to initiate roots.*—Approximately 7–14 days with the shorter times generally being experienced in the summer and the longer times in the winter.

*Time to develop roots.*—Approximately 21 days.

*Root description.*—Fine, fibrous.

*Rooting habit.*—Freely branching.

Plant description:

*Habit of growth.*—Compact, with good basal branching. A mature plant, 8 weeks after the planting of a rooted cutting, commonly measures approximately 22.1 cm in height and approximately 36.6 cm in width (plant spread).

*Plant form.*—Upright and mounded.

*Lateral branches.*—Quantity: Approximately 3 per plant. Length: Approximately 19.3 cm. Diameter: Approximately 1.1 cm. Texture: Glabrous. Color: 144D with streaks of 59A. Internode length: Approximately 1.6 cm.

*Foliage.*—Type: Simple. Arrangement: Alternate. Shape: Ovale. Apex: Cuspidate/Acuminate. Base: Attenuate. Margin: Crenate/ciliate. Texture: Glabrous. Venation pattern: Pinnate, arcuate. Size of mature foliage: Length: Approximately 2.9 cm. Width: Approximately 1.6 cm. Color of young and mature foliage: Upper surface is closest to 137A, with veins and mid-vein of 144C. Lower surface is closest to 138B with splotches of 184A and veins and mid-vein of 144C. Petiole: Length: Approximately 7.4 mm. Petiole diameter: 1.3 mm. Petiole texture: Both surfaces are glabrous. Petiole color: Upper and lower surfaces are 144C.

Flowering description:

*Flowering habit.*—Freely flowering.

*Natural flowering season.*—Year round in greenhouse environment. Flowering is continuous from spring until fall in the garden.

*Lastingness of individual bloom.*—Approximately 5–7 days.

*Quantity of flowers.*—Approximately 48 flowers and 15 buds per stem at any one time.

*Flower bud rate of opening.*—Generally it takes 7–10 days for buds to progress from first color to fully opened flowers.

*Mature flower buds (just before opening).*—Shape: Ovoid. Length: Approximately 8 mm. Diameter: Approximately 4 mm. Color of petals: N57C.

*Flower description.*—Type: Single. Shape: Round. Diameter: Approximately 2.3 cm. Depth: Approximately 3.3 mm. Borne: Above foliage arising from leaf axils and facing upward or outward. Flowers are not persistent or fragrant.

*Petals.*—Arrangement: Non imbricate. Number per flower: Approximately 5. Shape: Obovate. Margin: Entire. Apex: Emarginate. Texture: Glabrous. Appearance: Iridescent. The lateral petals overlap the lower petals and the two lower petals overlap each other.

*Superior petal.*—Size: Length: 7 mm. Width: 9 mm. Base: Truncate.

*Lateral petals.*—Length: 9 mm. Width: 6 mm. Base: Attenuate.

*Lower petals.*—Length: 1 cm. Width: 5 mm. Base: Attenuate.

*Flower color.*—Upper surface of fully opened petals: N57A. Lower petals have bases of 59B. Lower surface of fully opened petals: N66D. Petal color fading to: N66B.

*Calyx.*—Quantity of sepals: Three, with lower sepal modified into a spur. Sepal apex: Acuminate. Sepal texture: Glabrous. Lateral sepal shape: Lanceolate. Lateral sepal length: Approximately 2 mm. Lateral sepal width: Approximately 1 mm. Lateral sepal color: Both surfaces are 145B with tip of 53C. Lower sepal shape: Ovate. Lower sepal length: Approximately 7 mm. Lower sepal width: Approximately 5 mm at widest point. Lower sepal color: Both surfaces are 145D with streaks of 53C and tip of 53C.

*Spur.*—Quantity: One per flower. Length: Approximately 2.4 cm. Diameter at base: Approximately 2 mm. Diameter at tip: Approximately 1 mm. Color: 48B with tip of 58A.

*Pedicel.*—Length: Approximately 1.1 cm. Diameter: Approximately 1 mm. Texture: Glabrous. Strength: Strong. Angle to stem: Acute. Color: 144C with streaks of 59B.

*Reproductive organs.*—Androecium: Five stamens, anthers are fused together forming one organ that surrounds the pistil. Filaments are free. Generally, the anthers shed pollen prior to the stigma becoming receptive. Filament color: 71C. Anther shape: Oval. Anther length: 2 mm. Anther color: 79B. Pollen amount: Sparse. Pollen color: 76D. Gynoecium: Pistil number: One per flower. Pistil length: 3.5 mm. Stigma length: 0.5 mm. Stigma color: Darker than 71A. Style length: 0.5 mm. Style color: 71B. Ovary length: 2.5 mm. Ovary diameter: Ovary color: 143A.

Seed and fruit development: Neither seed nor fruit production has been observed.

Disease and pest resistance: Resistance to pathogens and pests common to Impatiens has not been observed.

What is claimed is:

1. A new and distinct cultivar of Impatiens plant named 'Balpixotse' substantially, as herein shown and described, which:

1. Exhibits single, pink-colored flowers,
2. Forms dark green-colored foliage,
3. Exhibits a good basal branching character, and
4. Exhibits a compact, upright and mounded growth habit.

* * * * *